United States Patent [19]

Kelm et al.

[11] Patent Number: 5,281,420
[45] Date of Patent: Jan. 25, 1994

[54] SOLID DISPERSION COMPOSITIONS OF TEBUFELONE

[75] Inventors: Gary R. Kelm; Douglas J. Dobrozsi, both of Cincinnati, Ohio

[73] Assignee: The Procter & Gamble Company, Cincinnati, Ohio

[21] Appl. No.: 885,932

[22] Filed: May 19, 1992

[51] Int. Cl.$^5$ .......................... A61K 9/20; A61K 9/48
[52] U.S. Cl. ................................. 424/452; 424/455; 424/465; 514/960; 514/962
[58] Field of Search ............... 514/962, 960, 210, 689; 424/452, 465

[56] References Cited

U.S. PATENT DOCUMENTS

| | | | |
|---|---|---|---|
| 2,698,822 | 1/1955 | Halpern et al. | 167/65 |
| 2,988,484 | 6/1961 | Barsky et al. | 167/82 |
| 3,308,217 | 3/1967 | Lowy et al. | 264/117 |
| 3,374,146 | 3/1968 | Blicharz et al. | 167/83 |
| 3,857,933 | 12/1974 | Ross et al. | 424/454 |
| 3,867,521 | 2/1975 | Miskel et al. | 424/37 |
| 4,151,273 | 4/1979 | Riegelman et al. | 514/462 |
| 4,156,719 | 5/1979 | Sezaki | 424/118 |
| 4,325,942 | 4/1982 | Taki | 424/94 |
| 4,344,934 | 8/1982 | Martin et al. | 424/501 |
| 4,450,877 | 5/1984 | Walker et al. | 141/1 |
| 4,454,152 | 6/1984 | Barry et al. | 424/456 |
| 4,690,816 | 9/1987 | Hata et al. | 424/456 |
| 4,690,823 | 9/1987 | Lohner et al. | 424/456 |
| 4,708,966 | 11/1987 | Loomans et al. | 514/689 |
| 4,786,495 | 11/1988 | Bird et al. | 424/81 |
| 4,795,643 | 1/1989 | Seth | 424/456 |
| 4,797,288 | 1/1989 | Sharma et al. | 424/476 |
| 4,827,062 | 5/1989 | Saeki et al. | 514/690 |
| 4,847,303 | 7/1989 | Loomans et al. | 549/689 |
| 4,849,428 | 7/1989 | Dobson et al. | 549/307 |
| 4,853,379 | 8/1989 | Shroot et al. | 514/179 |
| 4,936,074 | 6/1990 | Graham | 424/454 |
| 5,071,643 | 12/1991 | Yu et al. | 424/456 |
| 5,085,033 | 2/1992 | Graham | 424/454 |

FOREIGN PATENT DOCUMENTS

| | | |
|---|---|---|
| 182007 | 5/1986 | European Pat. Off. |
| 253490 | 1/1988 | European Pat. Off. |
| 371466 | 6/1990 | European Pat. Off. |
| 0431659 | 6/1991 | European Pat. Off. ..... A61K 31/12 |
| 1598458 | 9/1981 | United Kingdom |

OTHER PUBLICATIONS

Griffen, W. C., "Classification of Surface-Active Agents by 'HLB'", Journal of the Society of Cosmetic Chemists, vol. 1, No. 5 (1949), pp. 311–326.

CTFA Cosmetic Ingredient Dictionary, Third Edition (1984), N. F. Estrin, P. A. Crosely & C. R. Haynes, Eds., The Cosmetic Toiletry and Fragrance Association, Inc., Washington, D.C., pp. 39–40 211, 238 & 247.

The National Formulary, 17th Edition (1990), The United States Pharmacopeial Convention, Inc., Rockville, Md., p. 1966.

Primary Examiner—Shep K. Rose
Attorney, Agent, or Firm—Milton B. Graff, IV; Jerry J. Yetter

[57] ABSTRACT

The subject invention relates to compositions in dosage form comprising a solid dispersion which is a solidified melt mixture consisting essentially of the following components:
(a) from about 15% to about 75% of tebufelone;
(b) from about 25% to about 65% of a poloxamer surfactant having a melting point of about 40° C. or greater, the poloxamer surfactant consisting essentially of a block copolymer having three polymer blocks, a middle block of poly(oxypropylene) with a molecular weight of from about 1450 daltons to about 6000 daltons, and end blocks of poly(oxyethylene), the end blocks being from about 50% to about 90% of the copolymer; and
(c) from 0% to about 60% of other components, wherein the other components are miscible with a melt mixture of components (a) and (b).

21 Claims, No Drawings

SOLID DISPERSION COMPOSITIONS OF TEBUFELONE

TECHNICAL FIELD

The subject invention involves novel pharmaceutical compositions containing tebufelone, a di-tert-butylphenol anti-inflammatory compound. More particularly, it involves such compositions dosed perorally which provide good bioavailability of the compound.

BACKGROUND OF THE INVENTION

Certain substituted di-tert-butylphenol derivatives are known to be effective as anti-inflammatory, analgesic and/or antipyretic agents. Of particular interest regarding the subject invention is tebufelone, 1-3,5-bis(1,1-dimethylethyl)-4-hydroxyphenyl-5-hexyn-1-one disclosed in U.S. Pat. No. 4,708,966 issued to Loomans, Matthews & Miller on Nov. 24, 1987. (The compound is termed 4-(5'-hexynoyl)-2,6-di-tert-butylphenol therein.) Related compounds are disclosed in U.S. Pat. No. 4,846,303 issued to Loomans, Matthews & Miller on Jul. 11, 1989 and U.S. Pat. No. 4,849,428 issued to Dobson, Loomans, Matthews & Miller on Jul. 18, 1989. Certain compositions of tebufelone are disclosed in European Patent Application No. 0,431,659 of Kelm & Bruns published Jun. 12, 1991.

It is an object of the subject invention to provide solid dispersion pharmaceutical compositions for peroral administration of tebufelone which provide good bioavailability of the compound.

SUMMARY OF THE INVENTION

The subject invention relates to compositions in dosage form comprising a solid dispersion which is a solidified melt mixture consisting essentially of the following components:
(a) from about 15% to about 75% of tebufelone;
(b) from about 25% to about 65% of a poloxamer surfactant having a melting point of about 40° C. or greater, the poloxamer surfactant consisting essentially of a block copolymer having three polymer blocks, a middle block of poly(oxypropylene) with a molecular weight of from about 1450 daltons to about 6000 daltons, and end blocks of poly(oxyethylene), the end blocks being from about 50% to about 90% of the copolymer; and
(c) from 0% to about 60% of other components, wherein the other components are miscible with a melt mixture of components (a) and (b).

DETAILED DESCRIPTION OF THE INVENTION

The drug active of interest regarding the subject invention is 1-3,5-bis(1,1-dimethylethyl)-4-hydroxyphenyl-5-hexyn-1-one having the chemical structure:

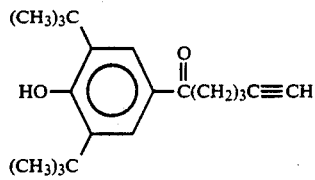

which is referred to herein as tebufelone. A method of synthesizing tebufelone is disclosed in aforementioned U.S. Pat. No. 4,708,966, which is hereby incorporated herein by reference.

The subject invention involves pharmaceutical compositions of tebufelone intended for peroral administration to humans and lower animals. The subject compositions comprise solid dispersions which comprise tebufelone and certain poloxamer surfactants. As used herein, "solid dispersion" means a material which is solid at specified temperatures, and which has been produced by blending melted tebufelone and poloxamer (and other components, if present), whereby a homogeneous melt mixture results, and cooling the resulting melt mixture so that it forms a solid with the components substantially uniformly dispersed therein.

The solid dispersions of the subject invention comprise from about 15% to about 75% tebufelone, preferably from about 25% to about 60% tebufelone; more preferably from about 35% to about 507. tebufelone. The melting point of tebufelone is about 70° C.

It has been found that tebufelone is essentially water-insoluble (solubility less than 1 μg/ml) and very lipophilic. The therapeutic dose of tebufelone is from about 10 mg to about 600 mg per day in humans. It has been found that the absorption of tebufelone from the gastrointestinal tract is quite low when the active is dosed in conventional dosage forms, where solid particles of substantially pure tebufelone are mixed with other solid excipients and filled into hard gelatin capsules or compressed into tablets. It has been found that good absorption of tebufelone from the gastrointestinal tract occurs only when the drug active is perorally administered in pharmaceutical compositions which provide rapid solubilization of the drug active in the gastrointestinal fluids. As used herein, being solubilized means that the drug active exists in an aqueous medium in a form that is freely diffusible. A free diffusible form is one that is capable of transversing the unstirred boundary layer present along the absorbing membrane of the gastrointestinal tract. Such freely diffusible forms include a pure aqueous solution of the drug active, an aqueous micellar solution of the drug active (drug molecules dissolved in surfactant micelles), and/or an emulsion of the drug active (liquid droplets containing drug actives surrounded by a surfactant layer dispersed in an aqueous medium).

It has been found that rapid solubilization of tebufelone in gastrointestinal fluids can be achieved from the compositions of the subject invention which comprise solid dispersions comprising tebufelone with certain poloxamer surfactants. The subject solid dispersions have melting points of about 40° C. or higher, preferably of from about 45° C. to about 100° C.; more preferably from about 50° C. to about 80° C.

The poloxamer surfactants useful in the compositions of the subject invention have melting points of about 40° C. or higher, yet have been found to provide the necessary solubilization of tebufelone. These poloxamer surfactants are block copolymers having three polymer blocks. The middle block of the copolymer is poly(oxypropylene) having a molecular weight of from about 1450 daltons to about 6000 daltons, preferably from about 1600 daltons to about 5000 daltons, more preferably from about 1750 daltons to about 4000 daltons. The end polymer blocks are poly(oxyethylene). The two poly(oxyethylene) end blocks together comprise at least about 50% of the weight of the block copolymer, preferably from about 50% to about 90%, more preferably from about 70% to about 80%. The average molecular weight of the block copolymer is from about 3000 to about 50,000, more preferably from about 4500 to about 25,000, most preferably from about 6500 to about 15,000. The melting point of the block copolymer is preferably from about 40° C. to about 80° C., more preferably from about 45° C. to about 60° C., most preferably from about 50° C. to about 60° C. Mixtures of suitable poloxamer surfactants can be used in the solid dispersions of the subject invention. The subject solid dispersions comprise from about 25% to about 65% of poloxamer surfactant, preferably from about 35% to about 50%.

Preferred examples of poloxamer surfactants useful in the solid dispersions of the subject invention include the following which are commercially available from BASF Wyandotte Corp., Parsippany, N.J.: Poloxamer 188 (Pluronic F68 ®), which is 80% poly(oxyethylene) and has a molecular weight of 8350 daltons and a melting point of 52° C.; Poloxamer 217 (Pluronic F77 ®), which is 70% poly(oxyethylene) and has a molecular weight of 6600 daltons and a melting point of 48° C.; Poloxamer 235 (Pluronic P85 ®), which is 50% poly(oxyethylene) and has a molecular weight of 4600 daltons and a melting point of 40° C.; Poloxamer 237 (Pluronic F87 ®), which is 70% poly(oxyethylene) and has a molecular weight of 7700 daltons and a melting point of 49° C.; Poloxamer 238 (Pluronic F88 ®), which is 80% poly(oxyethylene) and has a molecular weight of 10800 daltons and a melting point of 54° C.; Poloxamer 288 (Pluronic F98 ®), which is 80% poly(oxyethylene) and has a molecular weight of 13500 daltons and a melting point of 55° C.; Poloxamer 235 (Pluronic P105 ®), which is 50% poly(oxyethylene) and has a molecular weight of 6500 daltons and a melting point of 42° C.; Poloxamer 338 (Pluronic F108 ®), which is 80% poly(oxyethylene) and has a molecular weight of 14000 daltons and a melting point of 57° C.; and Poloxamer 407 (Pluronic F127 ®), which is 70% poly(oxyethylene) and has a molecular weight of 12500 daltons and a melting point of 56° F.

Solid dispersions of the subject invention may also include other components which are miscible with the tebufelone/poloxamer surfactant melt mixture. As used herein, being "miscible" with the tebufelone/poloxamer surfactant melt mixture means that the other components can be melted and mixed with the tebufelone/poloxamer surfactant melt mixture to form a homogeneous melt mixture, or the other components dissolve in the tebufelone/poloxamer melt mixture to form a homogeneous mixture. Other components of the solid dispersions of the subject invention are limited to those that result in the solid dispersion having a melting point of about 40° C. or higher, as provided hereinabove.

Examples of other components which are suitable for incorporation in the solid dispersions of the subject invention include other surfactants, and certain low molecular weight water-soluble materials. Preferred other surfactants include polysorbates (polyoxyethylene sorbitan fatty acid esters), polyoxyethylene alkyl ethers, polyoxyethylene castor oil derivatives, and polyoxyethylene stearates. Such other surfactants preferably have an HLB (hydropholic-lipophilic balance) greater than about 14. Polysorbates are included in the solid dispersions of the subject invention at levels of from 0% to about 60%, preferably from about 20% to about 40%; other surfactants are included at levels of from 0% to about 20%.

Preferred polysorbates useful in the solid dispersions of the subject invention include the following which are available commercially from ICI Americas, Inc., Stratford, Conn.: Polysorbate 20 (Tween 20 ®) having an HLB of 16.7, Polysorbate 40 (Tween 40 ®) having an HLB of 15.6, Polysorbate 60 (Tween 60 ®) having an HLB of 14.9, and Polysorbate 80 (Tween 80 ®) having an HLB of 15.0.

Preferred polyoxyethylene alkyl ethers include those sold under the trade name Brij ® available commercially from ICI Americas, Inc. Preferred polyoxyethylene castor oil derivatives include those sold under the trade name Cremophor ®, e.g., RH 40 and RH 60, available commercially from BASF Wyandotte Corp., Parsippany, N.J. Preferred polyoxyethylene stearates include those sold under the trade name Emerest ® available commercially from Emery Industries, Inc., Linden, N.J.

Another preferred additional component of the solid dispersions of the subject invention is a polyethylene glycol (PEG). PEGs are condensation polymers of ethylene oxide. Preferred PEGs are those with nominal molecular weights in excess of about 1500 daltons, preferably from about 2000 to about 20,000 daltons, more preferably from about 3000 daltons to about 8000 daltons. Examples include PEGs available commercially from Union Carbide Corp., Jacksonville, Fla. under the trade name Carbowax ®. PEGs are incorporated in the subject solid dispersions at levels of from 0% to about 60%, preferably from about 20% to about 40%.

Preferred solid dispersions of the subject invention consist essentially of tebufelone and poloxamer; tebufelone, poloxamer and polysorbate; tebufelone, poloxamer and PEG; or tebufelone, poloxamer, polysorbate and PEG; the quantity of each component being that disclosed hereinabove.

Other excipients which can be incorporated in the solid dispersions of the subject invention include urea (preferably from 0% to about 20%) and dextrose monohydrate (preferably from 0% to about 20%).

Solid dispersions of the subject invention are preferably made by melting the tebufelone and the poloxamer surfactant together, with mixing, to form a homogeneous melt mixture. Solid dispersions of the subject invention are made by cooling this binary melt mixture and allowing it to solidify. Other sol id dispersions of the subject development are made by adding other components to the binary melt mixture, mixing to form a homogeneous melt mixture, and cooling the resulting melt mixture to solidify it.

Preferred dosage form compositions of the subject invention are made from the above solid dispersions. Preferred solid dispersions of the subject invention can be formed into flowable particles by suitable means. The particles are then formulated into conventional dosage forms, such as tablets and capsules. Suitable means of producing the particles include oscillating screen size reduction of solidified melt mixtures and prilling of the melt.

An especially preferred dosage form consists of a hard gelatin capsule into which the homogeneous melt mixture is filled and allowed to solidify in situ. Another dosage form composition is made by filling the melt mixture into soft, elastic gelatin capsules. Another dosage form is made by forming molded tablets, e.g., by filling the melt mixture into tablet molds, or shaping partially solidified melt mixture into tablet shapes.

EXAMPLES

The following are non-limiting examples of compositions of the subject invention.

Example 1

| Tebufelone | 50% |
| --- | --- |
| Poloxamer 407 | 50% |

The two components are melted at 75° C. to form a homogeneous liquid which is allowed to solidify at ambient temperature. The resulting solid is milled using an oscillating screen to particle size of about 230 to 860 $\mu$m. The particles are filled into hard gelatin capsules using conventional capsule filling equipment.

Example 2

| Tebufelone | 40% |
| --- | --- |
| Poloxamer 238 | 40% |
| Polysorbate 80 | 20% |

Tebufelone and Poloxamer 238 are melted at 75° C. to form a homogeneous liquid to which Polysorbate 80 is added with mixing. The resulting melt mixture is filled into hard gelatin capsules using modified capsule filling equipment and allowed to solidify.

Example 3

| Tebufelone | 20% |
| --- | --- |
| Poloxamer 338 | 40% |
| Polysorbate 80 | 40% |

Tebufelone and Poloxamer 338 are melted at 85° C. to form a homogeneous liquid to which Polysorbate 80 is added with mixing. The resulting melt mixture is filled into hard gelatin capsules using modified capsule filling equipment and allowed to solidify.

Example 4

| Tebufelone | 30% |
| --- | --- |
| Poloxamer 338 | 30% |
| PEG (MW = 20,000) | 40% |

The three components are melted at 85° C. and blended to form a homogeneous liquid which is filled into standard suppository molds and allowed to solidify into molded tablets.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A composition comprising a solid dispersion which is a solidified homogeneous melt mixture comprising the following components:
   (a) from about 15% to about 75% of tebufelone;
   (b) from about 25% to about 65% of a poloxamer surfactant having a melting point of about 40° C. or greater, the poloxamer surfactant consisting essentially of a block copolymer having three polymer blocks, a middle block of poly(oxypropylene) with a molecular weight of from about 1450 to about 6000 daltons, and end blocks of poly(oxyethylene), the end blocks being from about 50% to about 90% by weight of the copolymer;
   wherein components of the solid dispersion are substantially uniformly dispersed therein.

2. A composition of claim 1 wherein the solid dispersion also comprises polyethylene glycol having a molecular weight of about 1500 or greater.

3. The composition of claim 2 wherein the polyethylene glycol has a molecular weight of from about 3000 to about 20,000, and comprises from about 20% to about 40% of the solid dispersion.

4. The composition of claim 1 wherein the solid dispersion also comprises a surfactant having an HLB of about 14 or greater.

5. The composition of claim 4 wherein the other surfactant is a polysorbate.

6. The composition of claim 5 wherein the polysorbate comprises from about 20% to about 40% of the solid dispersion.

7. The composition of claim 1 wherein the poloxamer surfactant has a melting point of from about 50° C. to about 80° C.

8. The composition of claim 7 wherein the poloxamer surfactant has a molecular weight of from about 6500 to about 15,000, and the end blocks are from about 60% to about 80% by weight of the copolymer.

9. The composition of claim 1 wherein the solid dispersion consists essentially of the tebufelone, the poloxamer surfactant, and of one or both of polysorbate and polyethylene glycol.

10. The composition of claim 9 wherein the polysorbate and polyethylene glycol comprise from about 20% to about 40% of the solid dispersion.

11. The composition of claim 1 wherein the poloxamer surfactant is selected from the group consisting of Poloxamer 188, Poloxamer 217, Poloxamer 235, Poloxamer 237, Poloxamer 238, Poloxamer 288, Poloxamer 235, Poloxamer 338, and Poloxamer 407.

12. The composition of claim 9 wherein the poloxamer surfactant is selected from the group consisting of Poloxamer 188, Poloxamer 217, Poloxamer 235, Poloxamer 237, Poloxamer 238, Poloxamer 288, Poloxamer 235, Poloxamer 338, and Poloxamer 407.

13. The composition of claim 5 wherein the polysorbate is selected from the group consisting of Polysorbate 20, Polysorbate 40, Polysorbate 60, and Polysorbate 80.

14. The composition of claim 12 wherein the polysorbate is selected from the group consisting of Polysorbate 20, Polysorbate 40, Polysorbate 60, and Polysorbate 80.

15. The composition of claim 14 wherein the polyethylene glycol has a molecular weight of from about 3000 to about 20,000.

16. The composition of claim 1 wherein the solid dispersion comprises from about 35% to about 60% of tebufelone.

17. The composition of claim 1 wherein the solid dispersion comprises from about 35% to, about 50% of the poloxamer surfactant.

18. The composition of claim 16 wherein the solid dispersion comprises from about 35% to about 50% of the poloxamer surfactant.

19. The composition of claim 14 wherein the solid dispersion comprises from about 35% to about 60% of tebufelone, and from about 35% to about 50% of the poloxamer surfactant.

20. The composition of claim 1 wherein the solid dispersion comprises about 20% tebufelone, about 40% Poloxamer 338, and about 40% Polysorbate 80.

21. A composition in dosage unit form comprising the solid dispersion of any of claims 1, 11, 15, 19 and 20, the dosage unit form being a hard gelatin capsule or a molded tablet.

* * * * *